US008691071B2

(12) United States Patent
Mayer et al.

(10) Patent No.: US 8,691,071 B2
(45) Date of Patent: Apr. 8, 2014

(54) COULOMETRIC ANALYTE SENSING INSTRUMENT WITH AN ANALYTE-CONSUMING SENSOR IN A CLOSED CELL

(75) Inventors: Daniel W. Mayer, Wyoming, MN (US); Stephen D. Tuomela, Ramsey, MN (US)

(73) Assignee: Mocon, Inc., Minneapolis, MN (US)

( * ) Notice: Subject to any disclaimer, the term of this patent is extended or adjusted under 35 U.S.C. 154(b) by 1011 days.

(21) Appl. No.: 12/114,471

(22) Filed: May 2, 2008

(65) Prior Publication Data

US 2010/0051481 A1  Mar. 4, 2010

(51) Int. Cl.
*G01N 27/404* (2006.01)

(52) U.S. Cl.
USPC ............. 205/775; 205/783; 205/788; 73/23.2

(58) Field of Classification Search
USPC ............. 73/19.01–31.07, 38; 205/775–794.5
See application file for complete search history.

(56) References Cited

U.S. PATENT DOCUMENTS

| | | | |
|---|---|---|---|
| 3,498,110 A | 3/1970 | Brun | |
| 3,524,341 A | 8/1970 | Roy | |
| 3,590,634 A * | 7/1971 | Pasternak et al. | 374/54 |
| 3,618,361 A | 11/1971 | Stephens et al. | |
| 4,563,249 A * | 1/1986 | Hale | 205/793 |
| 4,656,865 A | 4/1987 | Callan | |
| 4,815,316 A | 3/1989 | Tantram | |
| 4,973,395 A | 11/1990 | Mayer et al. | |
| 5,053,116 A | 10/1991 | Mayer | |
| 5,131,261 A | 7/1992 | Tou et al. | |
| 5,265,463 A | 11/1993 | Loebig | |
| 5,390,539 A | 2/1995 | Mayer | |
| 5,513,515 A | 5/1996 | Mayer | |
| 5,591,898 A | 1/1997 | Mayer | |
| 5,939,617 A | 8/1999 | Lim et al. | |
| 6,009,743 A * | 1/2000 | Mayer | 73/38 |
| 6,360,588 B1 | 3/2002 | Ross et al. | |
| 6,387,329 B1 | 5/2002 | Lewis et al. | |
| 6,766,682 B2 | 7/2004 | Engle et al. | |

FOREIGN PATENT DOCUMENTS

JP   62-119433   5/1987

OTHER PUBLICATIONS

Orchard, G.A.J et al., Oxygen and Water-Vapor Diffusion Through Biaxially Oriented Poly (ethylene terephthalate), Journal of Polymer Science: Part B: Polymer Physics, vol. 28, 603-621 (1990).

* cited by examiner

*Primary Examiner* — Alex Noguerola
(74) *Attorney, Agent, or Firm* — Sherrill Law Offices, PLLC

(57) ABSTRACT

A method for measuring the transmission rate of an analyte through a film. The method includes the steps of (i) separating a chamber into a first cell and a second cell with a known area of a film, (ii) flushing the first cell with an inert gas to remove any target analyte from the first cell, (iii) introducing a gas containing a known concentration of an analyte into the second cell, (iv) sealing the first cell to gas flow through the first cell, and (v) sensing any analyte in the first cell with a sensor that consumes the analyte at a rate greater than the rate at which the analyte is passing through the film, until a steady state rate of analyte consumption is measured by the sensor.

16 Claims, 19 Drawing Sheets

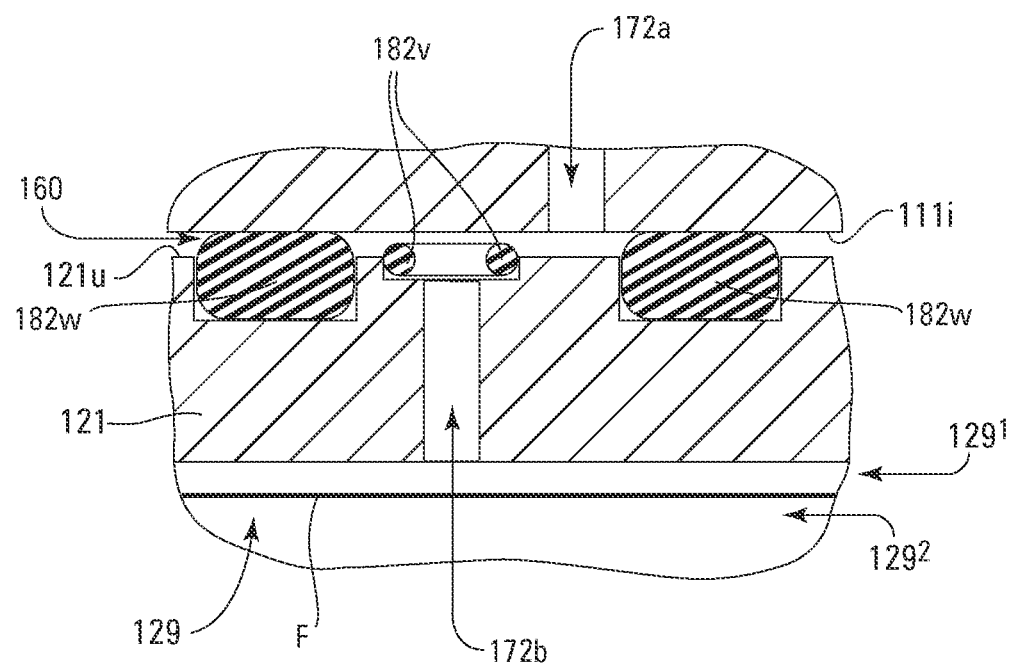
Fig. 4A²

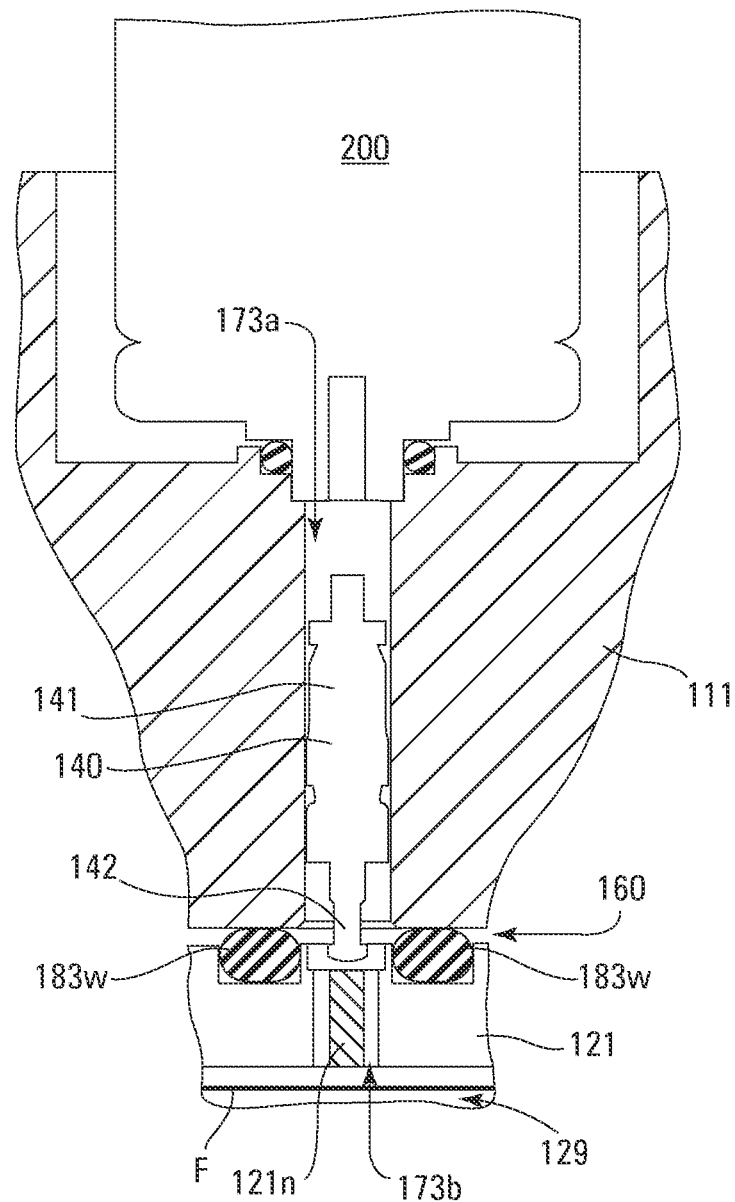
Fig. 4A³

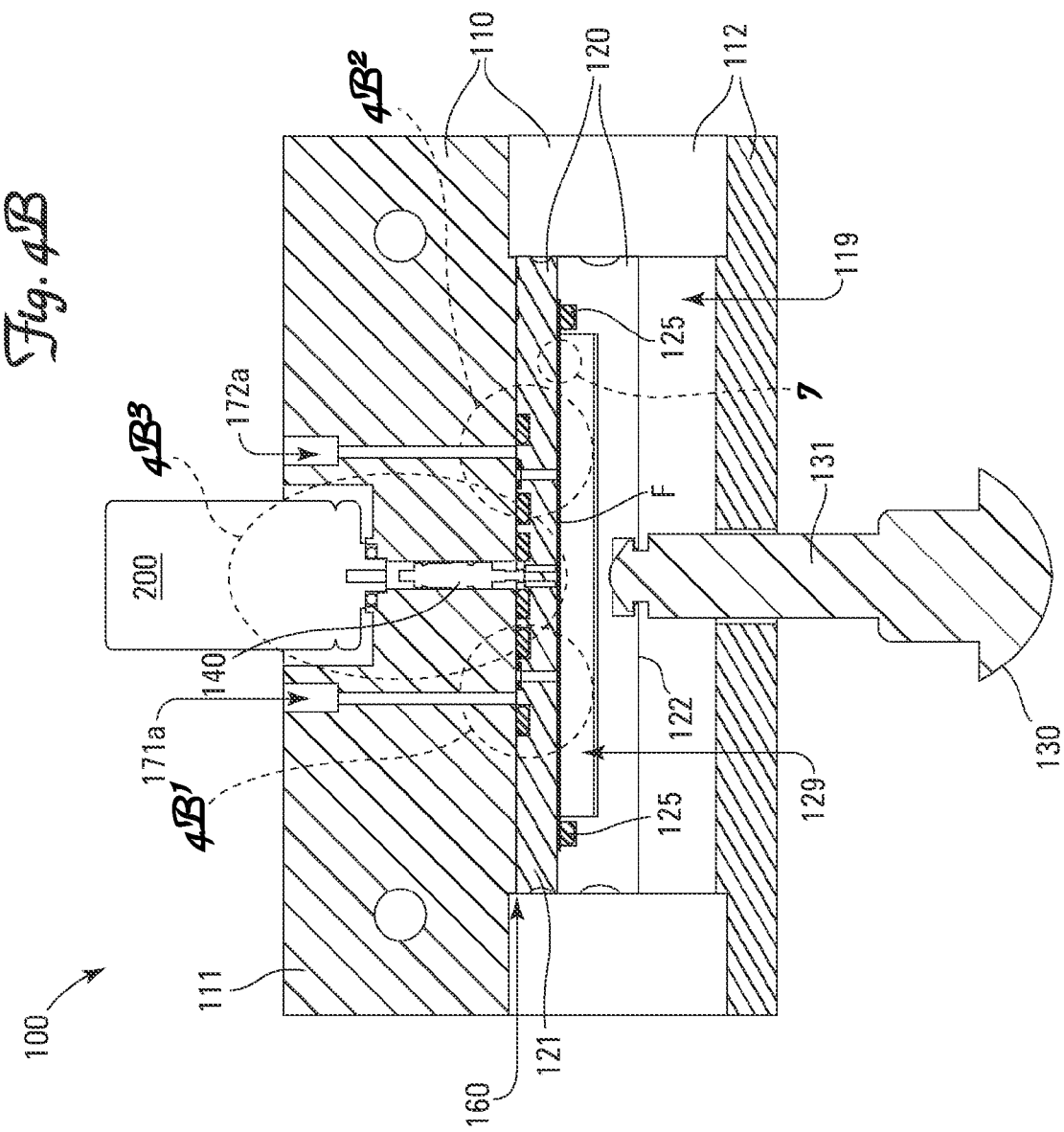

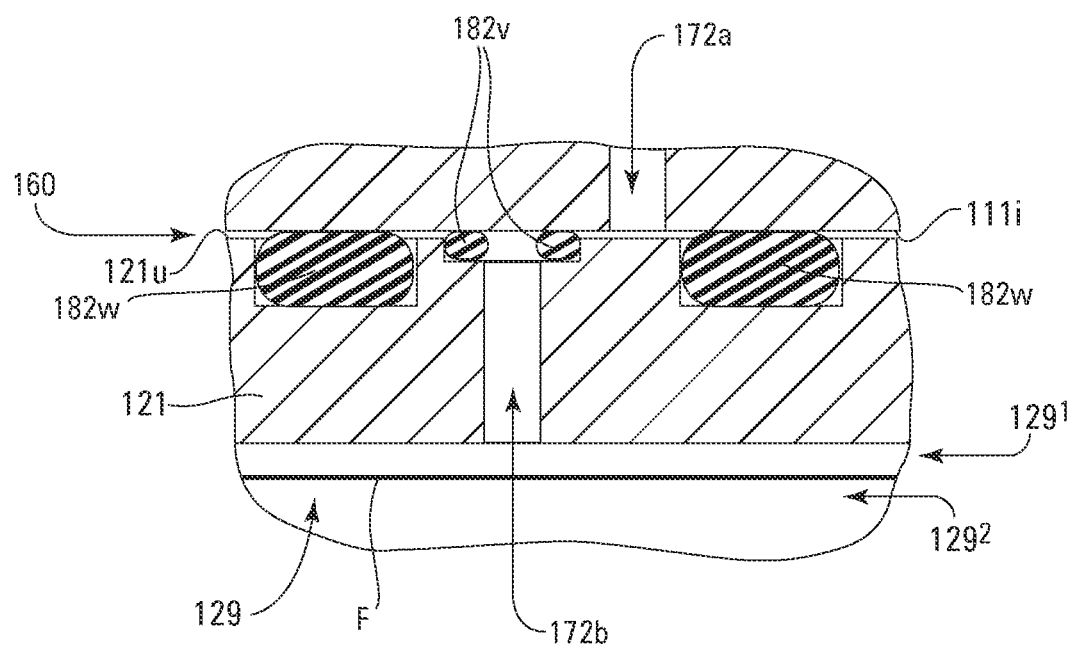
Fig. 4B²

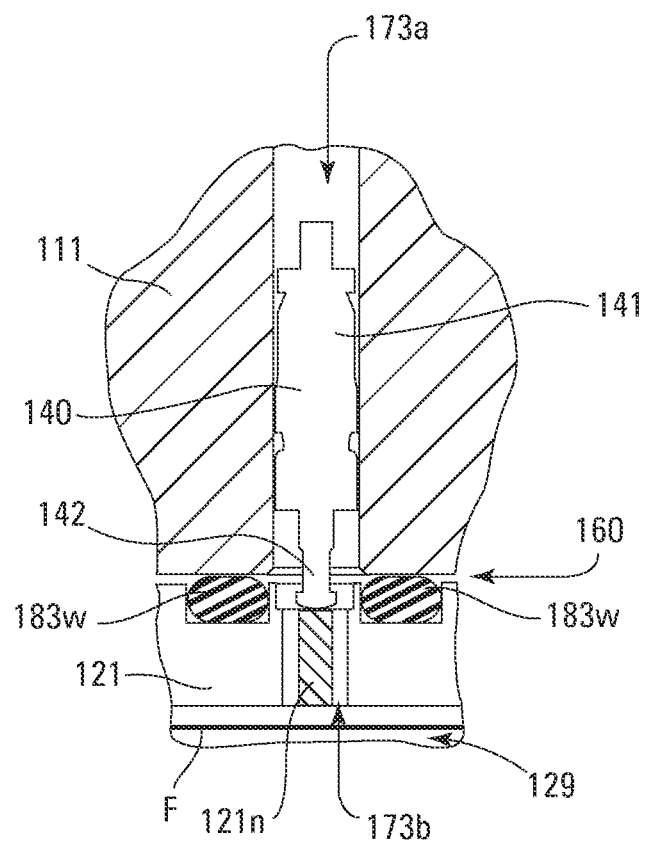
Fig. 4B³

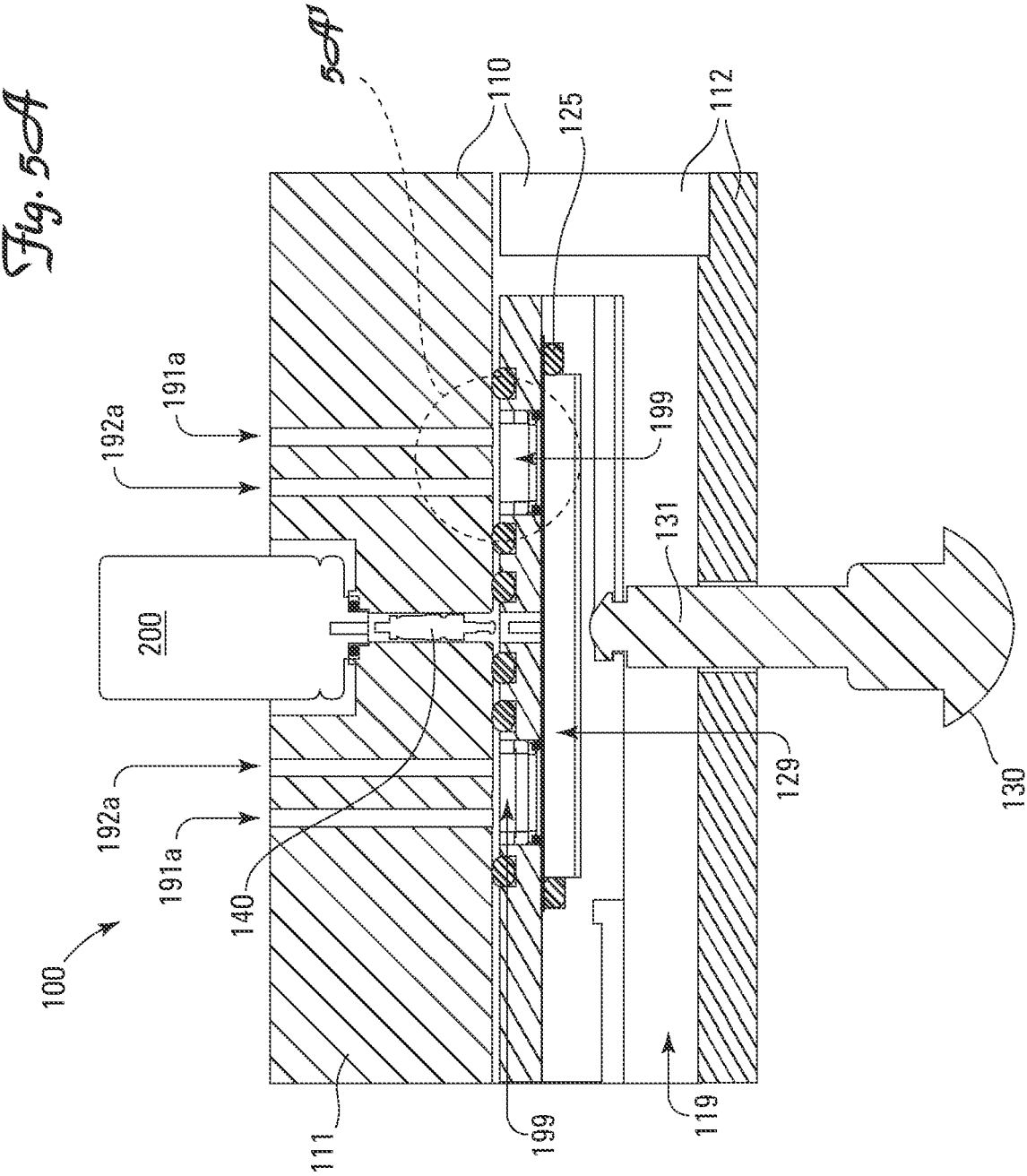

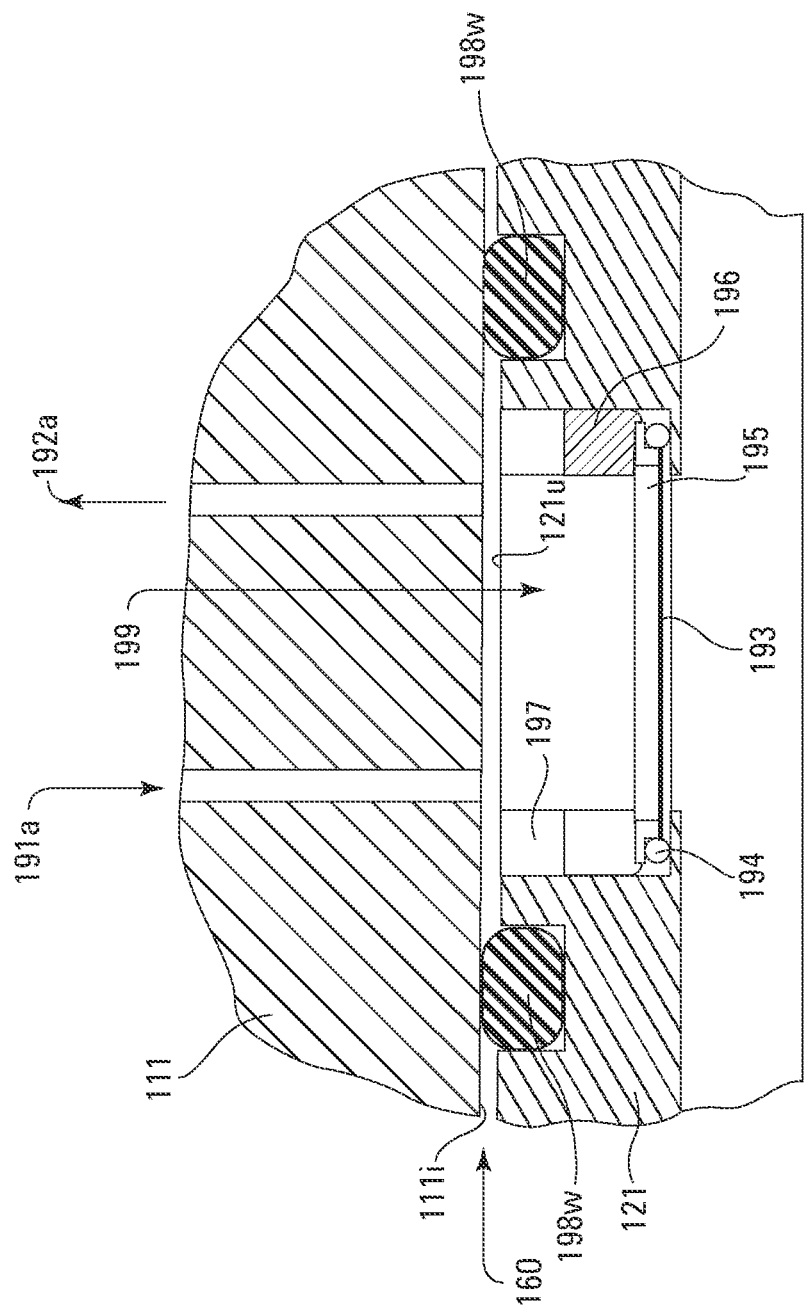

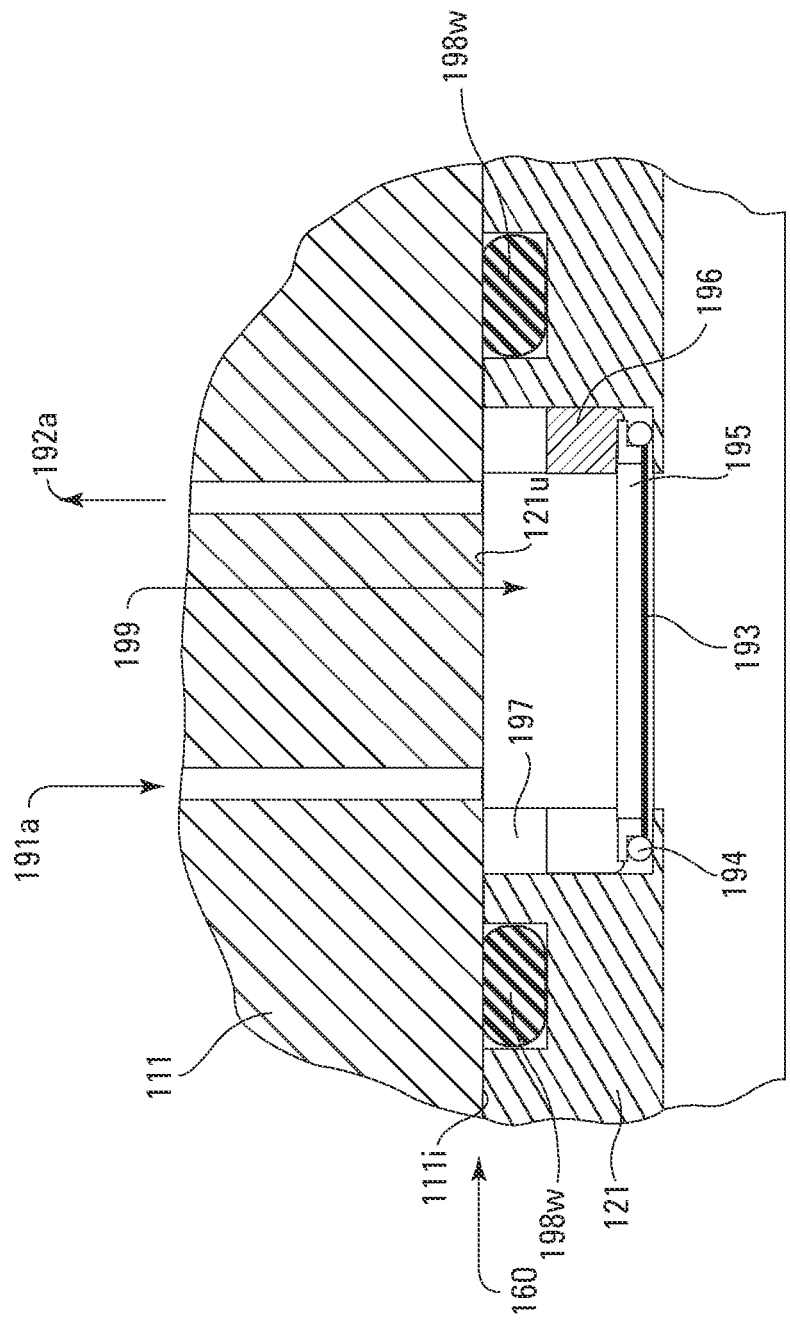

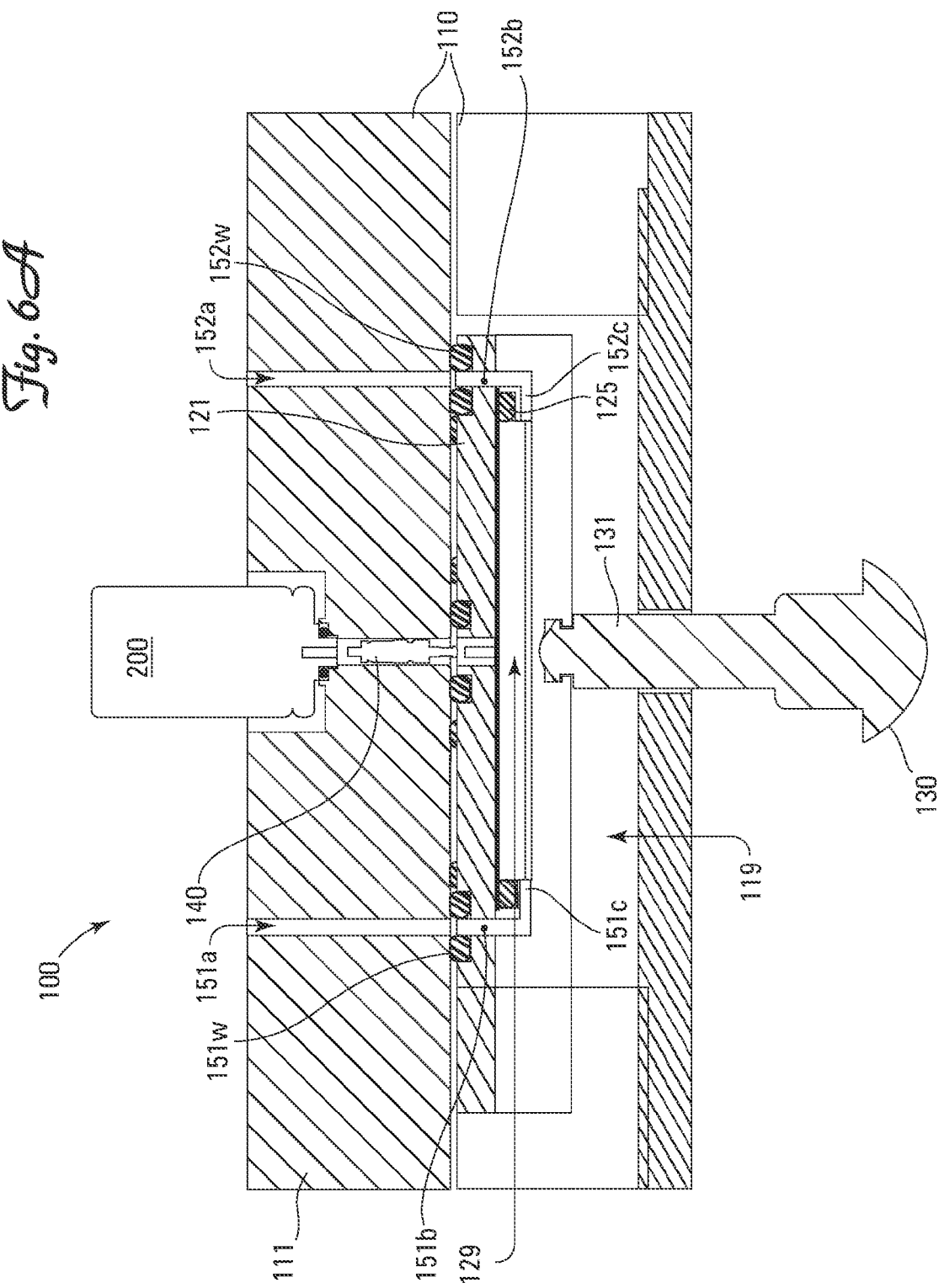

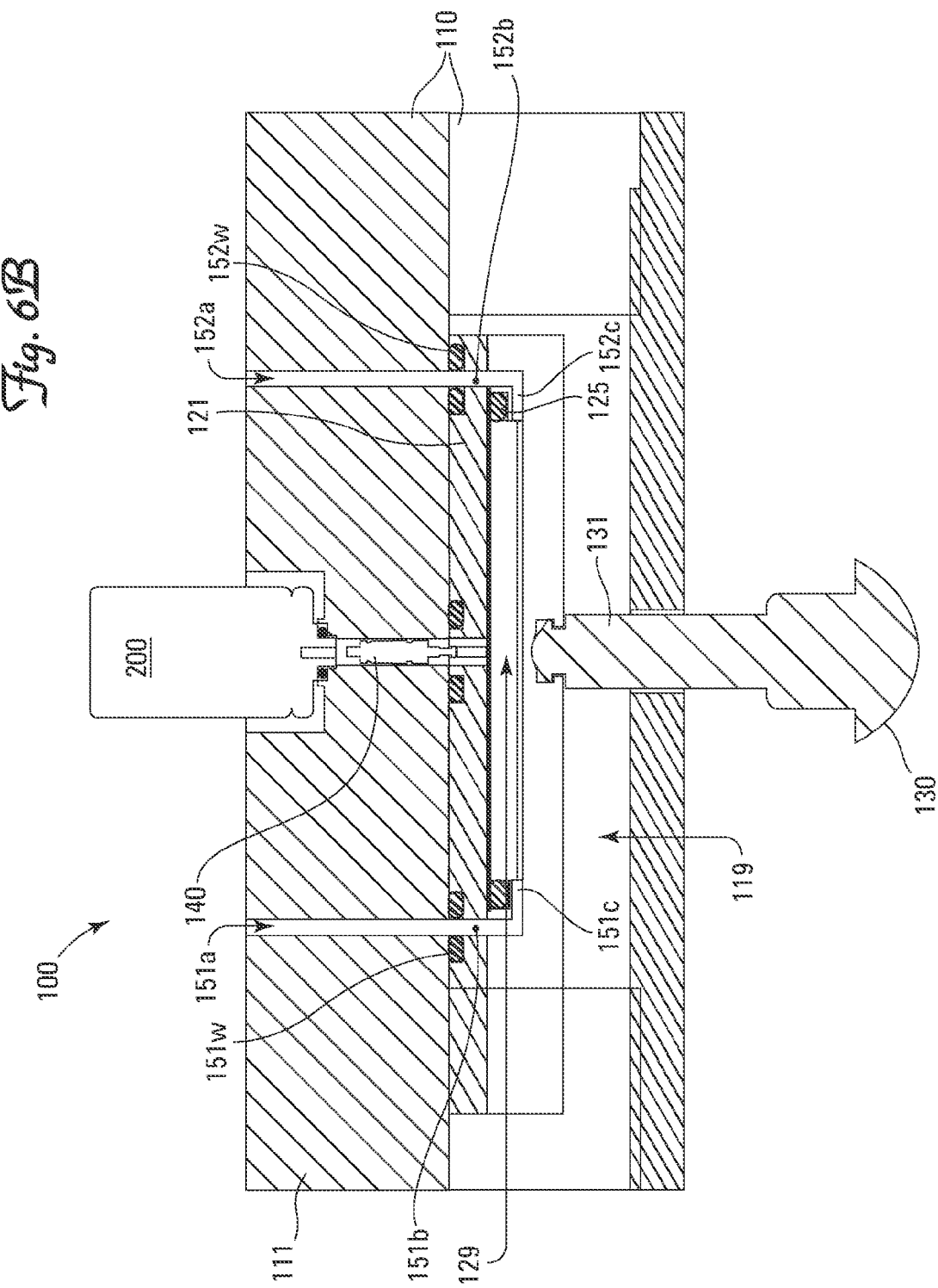

COULOMETRIC ANALYTE SENSING INSTRUMENT WITH AN ANALYTE-CONSUMING SENSOR IN A CLOSED CELL

BACKGROUND

Permeation instruments are used to measure the transmission rate of a target analyte, such as oxygen, carbon dioxide or water vapor, through a film of interest. Typical films subjected to permeation testing are polymeric packaging films such as those constructed from low density polyethylene (LDPE), high density polyethylene (HDPE), oriented polypropylene (OPP), polyethylene terepthalate (PET), polyvinylidene chrloride (PVTDC), etc. Typically, the film to be tested is positioned within a test chamber to sealing separate the chamber into first and second cells. The first cell (commonly referenced as the sensing cell) is flushed with an inert gas to remove any target analyte from the cell and the second cell (commonly referenced as the analyte cell) filled with a gas containing a known concentration of the target analyte. A sensor for the target analyte detects the presence of target analyte that has migrated into the first cell from the second cell through the film.

Permeation instruments typically employ a flow-through method or an accumulation method for sensing the presence of target analyte in the first cell. Briefly, the flow-through method uses an inert flushing gas to continuously pick up any target analyte that has migrated into the first cell and deliver it to a remote sensor. The accumulation method allows target analyte to build up in the first cell for an accumulation period, with the sensor either positioned within the first cell or the first cell flushed with a flushing gas after the accumulation period for delivery of accumulated target analyte to a remote sensor.

The flow through method allows virtually all sensor types to be used, but are expensive and complex systems. The accumulation method, while permitting the use of less sensitive inexpensive sensors to accurately measure permeation of a target analyte through a film even at very low transmission rates, suffers from significantly longer test times.

Coulometric sensors are sensors that follow Faraday's Law, and are generally preferred for use in permeation instruments as they provide a number of advantages, including (i) extreme accuracy, (ii) elimination of any need to calibrate, (iii) ultra-high sensitivity to analyte, (iv) high specificity for a single analyte, (v) lack of temperature sensitivity, (vi) lack of pressure sensitivity, (vii) minimal sensitivity to flow, and (viii) low cost.

Most coulometric sensors are electrochemical. Unfortunately, electrochemical sensors are susceptible to the rapid loss of electrolyte to the surrounding environment, resulting in a rapid decline in sensitivity and a short useful life. The traditional method to solve this problem is to limit environmental access to the electrolyte by covering the sensor with a selective membrane that allows essentially unrestricted passage of the target analyte while limiting the passage of water molecules, or permitting access to the electrolyte only through a limited number of capillary columns. While effective for reducing the loss of electrolyte and thereby increasing the useful life of the sensor, such covered sensors suffer from a 100 to 1000 times reduction in sensitivity and a concomitant loss of all the coulometric sensor benefits described above, with the single exception of low cost.

Such covered electrochemical sensors are not widely used with permeation instruments employing the flow-through method as they do not possess the necessary sensitivity, and are not widely used with permeation instruments employing the accumulation method because they consume some of the target analyte during the measurement process, requiring complex corrective calculations in an imperfect effort to "correct" the sensed data.

It is possible to design and construct a coulometric sensor that doesn't suffer from the rapid lose electrolyte or sensitivity, See, U.S. Pat. Nos. 4,973,395 and 5,053,116, but such sensors are prohibitively expensive for use in low-cost permeation testing instruments.

Accordingly, a substantial need exists for a permeation instrument that enjoys the benefits achievable by using a coulometric sensor without suffering from the limited useful life inherent with electrochemical sensors.

SUMMARY OF THE INVENTION

The invention is directed to a method for measuring the transmission rate of an analyte through a film. The method includes the steps of (i) separating a chamber into a first cell and a second cell with a known area of a film, (ii) flushing the first cell with an inert gas to remove any target analyte from the first cell, (iii) introducing a gas containing a known concentration of an analyte into the second cell, (iv) sealing the first cell to gas flow through the first cell, and (v) sensing any analyte in the first cell with a sensor that consumes the analyte at a rate greater than the rate at which the analyte is passing through the film, until a steady state rate of analyte consumption is measured by the sensor.

So long as the rate of consumption of analyte by the sensor is greater than the transmission rate of analyte through the film, the sensor is able to essentially measure all analyte passing through the film into the first cell. Once equilibrium is reached, the analyte transmission rate measured by the sensor will remain substantially constant, with this steady-state current, which follows Faraday's Law, equating to the analyte transmission rate of the film. Since the transmission rate of analyte through most films of interest tends to be magnitudes lower than the rate at which analyte is consumed by typical covered electrochemical sensors, the instrument may employ standard, low cost, porous or nonporous membrane-covered electrochemical analyte sensors while achieving the functionality and benefits of a coulometric sensor.

Figure 4A:
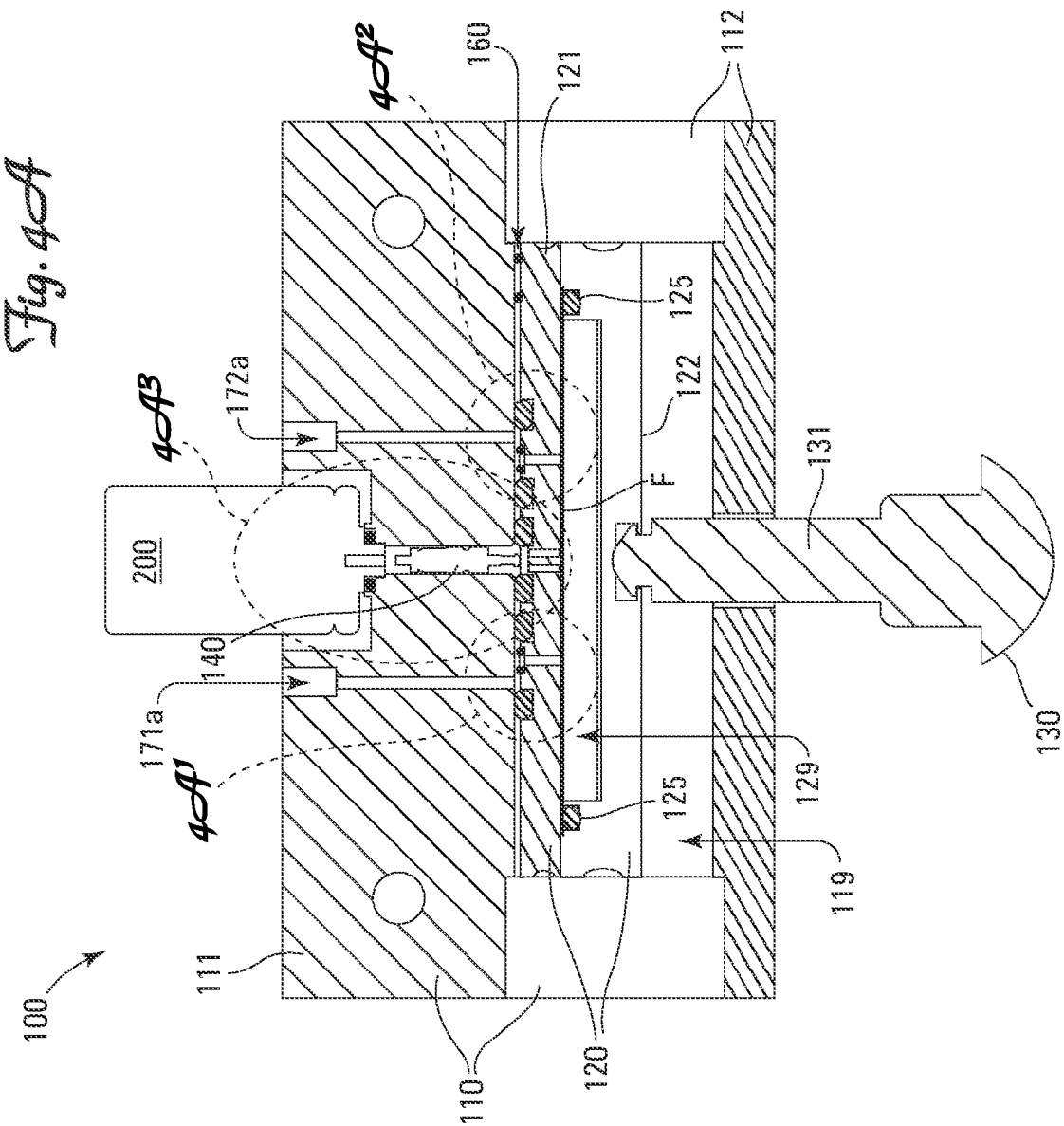
FIG. 4A is a cross-sectional side view of the measurement unit shown in FIG. 3 taken along line 4-4 with the upper mounting plate in the open position spaced a distance away from the upper portion of the housing.

FIG. $4A^1$ is an enlarged cross-sectional side view of the encircled inlet area of the gap in the measurement unit shown in FIG. 4A.

FIG. $4A^2$ is an enlarged cross-sectional side view of the encircled outlet area of the gap in the measurement unit shown in FIG. 4A.

FIG. $4A^3$ is an enlarged cross-sectional side view of the encircled sensor passageway area of the gap in the measurement unit shown in FIG. 4A.

Figure 3:
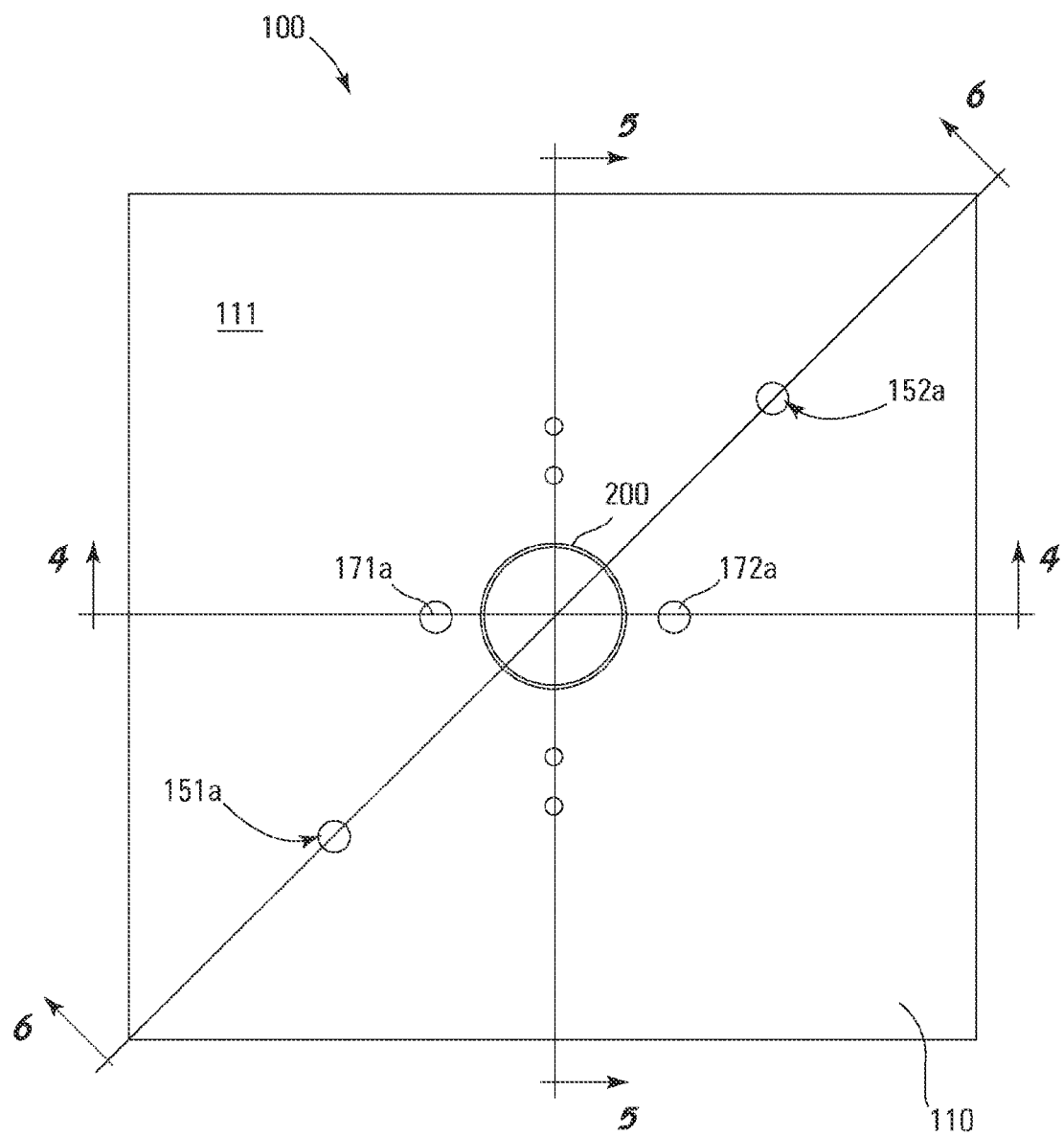
FIG. 3 is a top view of the measurement unit component of the testing system shown in FIG. 2.
Figure 4A:
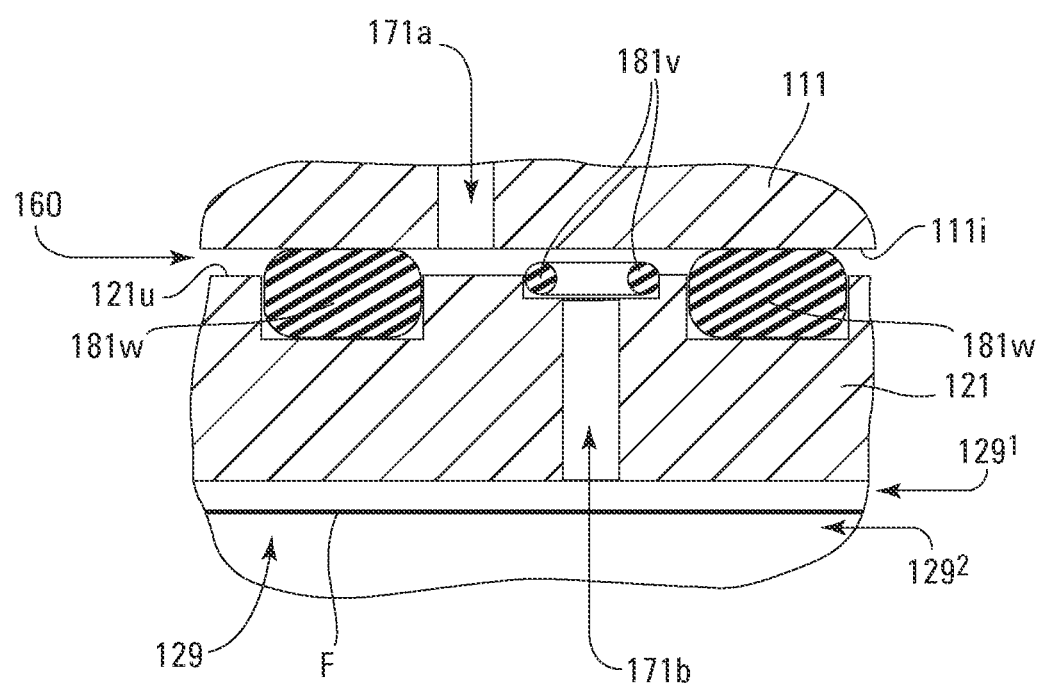
Figure 4B:
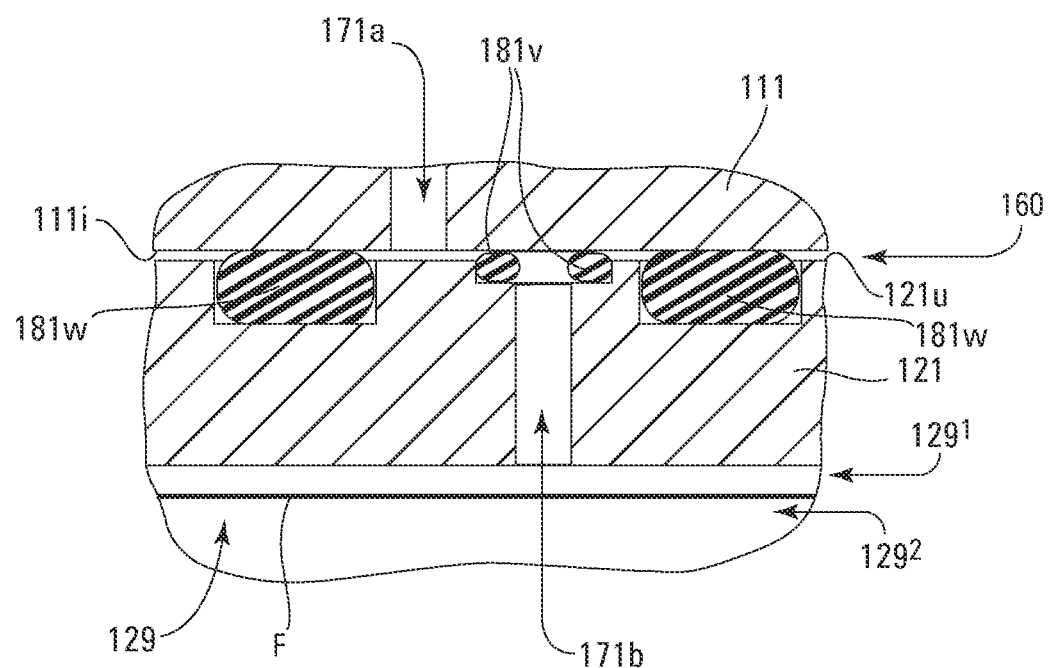

FIG. 4B is a cross-sectional side view of the measurement unit shown in FIG. 3 taken along line 4-4 with the upper mounting plate in the closed position immediately adjacent the upper portion of the housing.

FIG. 4B$^1$ is an enlarged cross-sectional side view of the encircled inlet area of the gap in the measurement unit shown in FIG. 4B.

FIG. 4B$^2$ is an enlarged cross-sectional side view of the encircled outlet area of the gap in the measurement unit shown in FIG. 4B.

FIG. 4B$^3$ is an enlarged cross-sectional side view of the encircled sensor passageway area of the gap in the measurement unit shown in FIG. 4B.

FIG. 5A is a cross-sectional side view of the measurement unit shown in FIG. 3 taken along line 5-5 with the upper mounting plate in the open position spaced a distance away from the upper portion of the housing.

FIG. 5A$^1$ is an enlarged cross-sectional side view of the encircled humidity control window in the measurement unit shown in FIG. 5A.

Figure 5B:
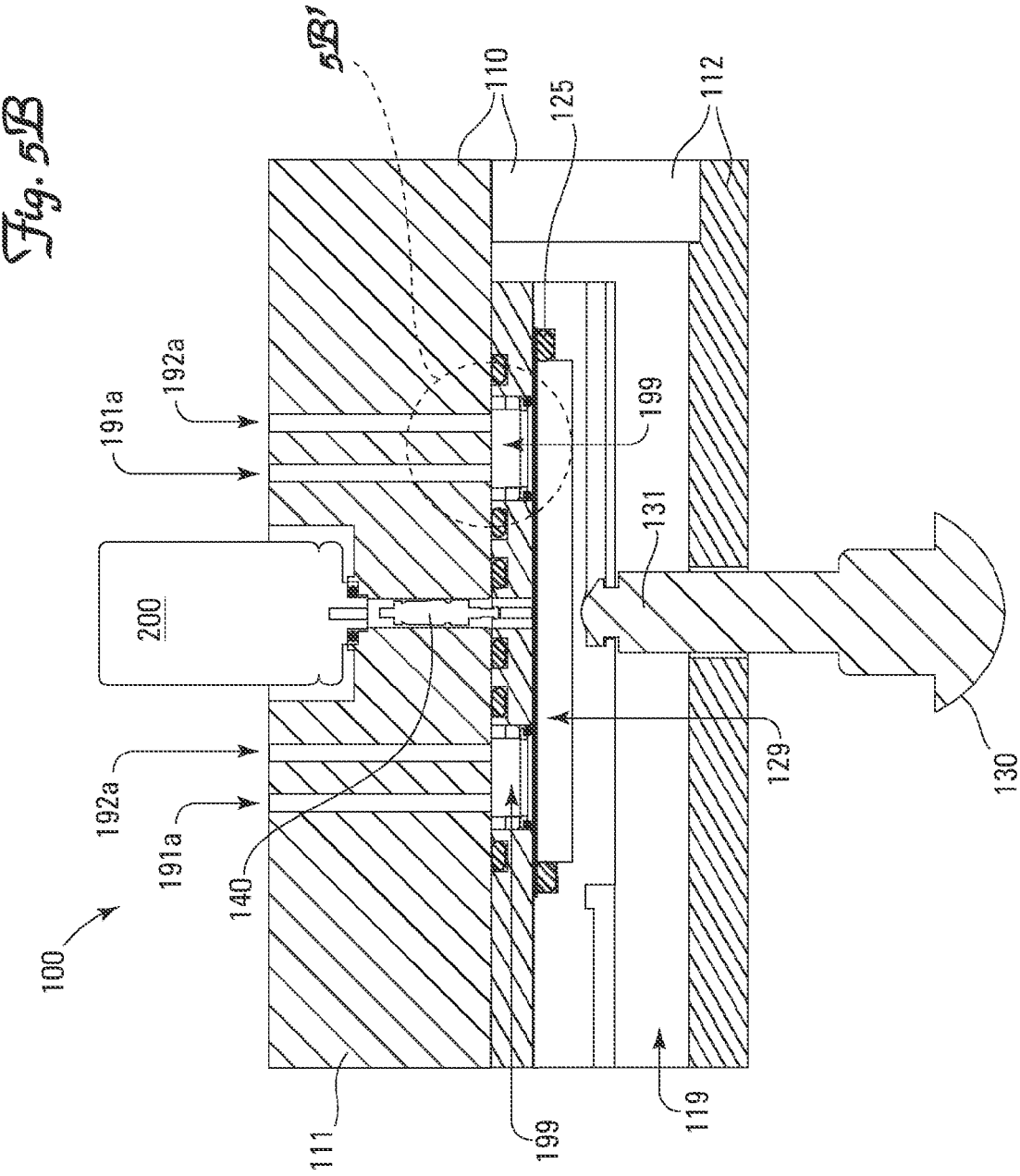

FIG. 5B is a cross-sectional side view of the measurement unit shown in FIG. 3 taken along line 5-5 with the upper mounting plate in the closed position immediately adjacent the upper portion of the housing.

FIG. 5B$^1$ is an enlarged cross-sectional side view of the encircled humidity control window in the measurement unit shown in FIG. 5B.

FIG. 6A is a cross-sectional side view of the measurement unit shown in FIG. 3 taken along line 6-6 with the upper mounting plate in the open position spaced a distance away from the upper portion of the housing.

FIG. 6B is a cross-sectional side view of the measurement unit shown in FIG. 3 taken along line 6-6 with the upper mounting plate in the closed position spaced a distance away from the upper portion of the housing.

Figure 7:
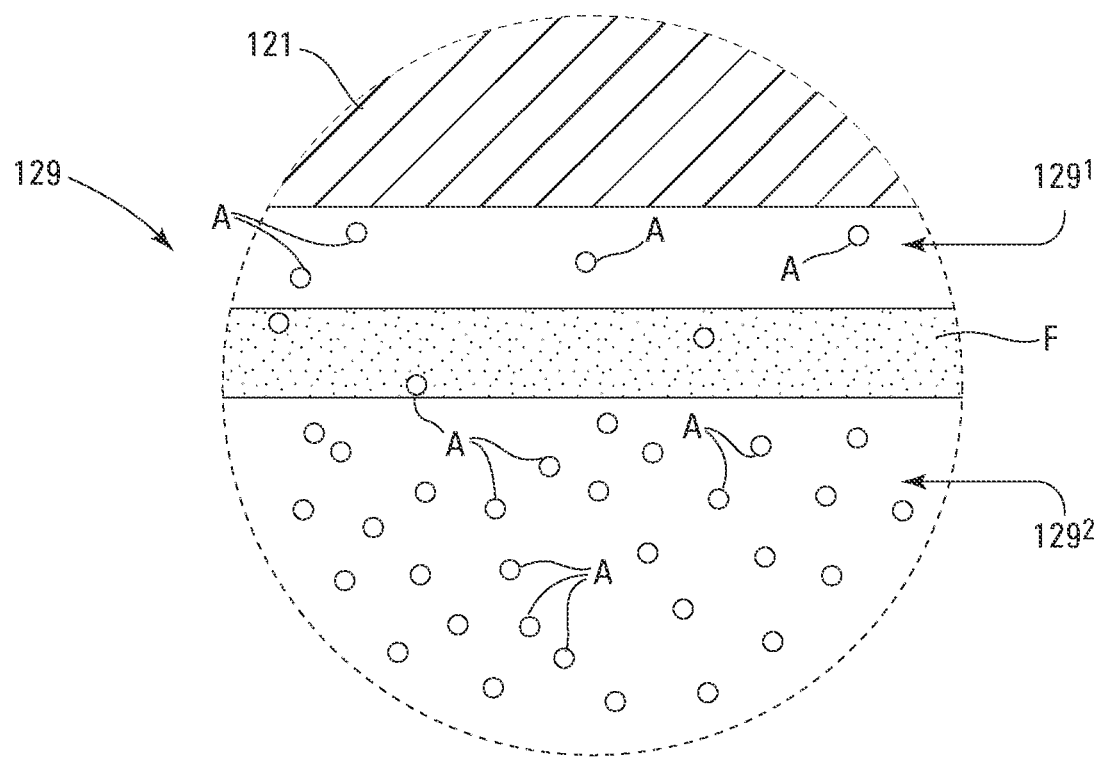

FIG. 7 is a grossly enlarged side view of the encircled portion of the testing chamber shown in FIG. 3 depicting individual molecules of an analyte of interest on each side of a test film being tested with the measurement unit shown in FIG. 4B.

Figure 8:
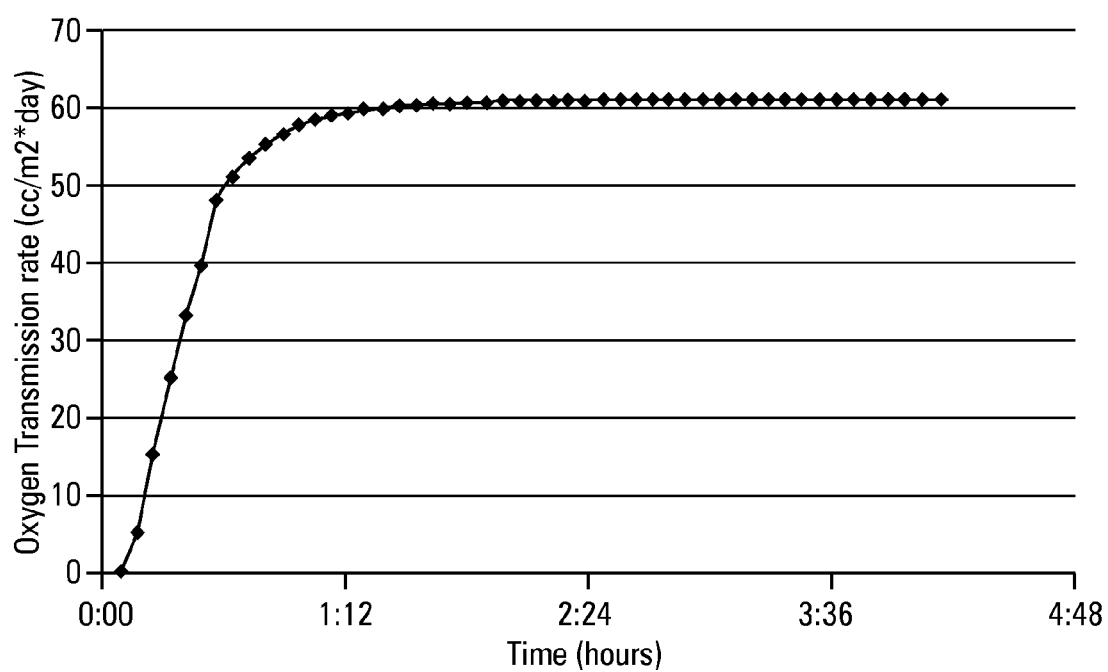

FIG. 8 is a graph of the $O_2$ transmission rate over time obtained from the permeation testing conducted in Example 1.

DETAILED DESCRIPTION OF A PREFERRED EMBODIMENT

Nomenclature

10 Testing System
21 Source of Inert Gas
22 Source of Test Gas
31a Inlet Shutoff Valve for Source of Inert Gas
31b Outlet Shutoff Valve for Source of Inert Gas
32a Inlet Shutoff Valve for Source of Test Gas
32b Outlet Shutoff Valve for Source of Test Gas
41a Inlet Conduit for Directing Gas From the Source of Inert Gas Into the Upper Cell
41b Outlet Conduit for Venting Gas From the Upper Cell
42a Inlet Conduit for Directing Gas From the Source of Test Gas Into the Lower Cell
42b Outlet Conduit for Venting Gas From the Lower Cell
50 Computer or CPU
60 Monitor
70 Printer
80 Electrical Leads from the Sensor to the CPU
100 Measurement Unit
110 Housing
111 Upper Section of Housing
111i Lower Surface of Upper Section of Housing
112 Lower Section of Housing
119 Retention Chamber Defined by Housing
120 Mounting Plates
121 Upper Mounting Plate
121u Upper Surface of Upper Mounting Plate
121n Pin On Upper Mounting Plate
122 Lower Mounting Plate
125 O-ring Between Mounting Plates
129 Testing Chamber Defined by Mounting Plates
129$^1$ Upper Cell of Testing Chamber
129$^2$ Lower Cell of Testing Chamber
130 Actuator
131 Actuator Shaft
140 Valve for Passageway to Analyte Sensor
141 Valve Body
142 Valve Stem
151a Inlet Channel to Lower Cell Through Upper Section of Housing
151b Inlet Channel to Lower Cell Through Upper Mounting Plate
151c Inlet Channel to Lower Cell Through Lower Mounting Plate
151w Larger O-ring within Gap Encircling Inlet Passageways into the Lower Cell
152a Outlet Channel from Lower Cell Through Upper Section of Housing
152b Outlet Channel from Lower Cell Through Upper Mounting Plate
152c Outlet Channel from Lower Cell Through Lower Mounting Plate
152w Larger O-ring within Gap Encircling Outlet Passageways from the Lower Cell
160 Gap Between Upper Section of Housing and Upper Mounting Plate
170 Flow Control Channels and Passageways Through the Upper Section of the Housing and the Upper Mounting Plate
171a Inlet Channel to Gap Through Upper Section of Housing
171b Inlet Channel from Gap to Upper Cell Through Upper Mounting Plate
172a Outlet Channel from Gap Through Upper Section of Housing
172b Outlet Channel from Upper Cell to Gap Through Upper Mounting Plate
173a Passageway from Gap to Analyte Sensor Through Upper Section of Housing
173b Passageway from Upper Cell to Gap Through Upper Mounting Plate
180 O-Ring Seals within the Gap
181v Smaller O-ring within Gap Encircling Inlet Channel through Upper Mounting Plate
181w Larger O-ring within Gap Encircling Both Inlet Channels
182v Smaller O-ring within Gap Encircling Outlet Channel through Upper Mounting Plate
182w Larger O-ring within Gap Encircling Both Outlet Channels
183w Larger O-ring within Gap Encircling Passageways Leading to the Sensor
190 Humidity Control System
191a Inlet Channel to Humidity Control Chamber Through Upper Section of Housing 192a Outlet Channel from Humidity Control Chamber Through Upper Section of Housing
193 Selectively Permeable Film
194 O-ring
195 Washer
196 Inset Ring
197 Locking Ring
198w Larger O-ring within Gap Encircling Both Inlet and Outlet Channels for a Humidity Control Chamber
199 Humidity Control Chambers in the Upper Mounting Plate
200 Analyte Sensor
A Analyte Molecules
F Film Being Tested
x Lateral Direction
y Longitudinal Direction
z Transverse Direction

Description

Overview

Figure 1:
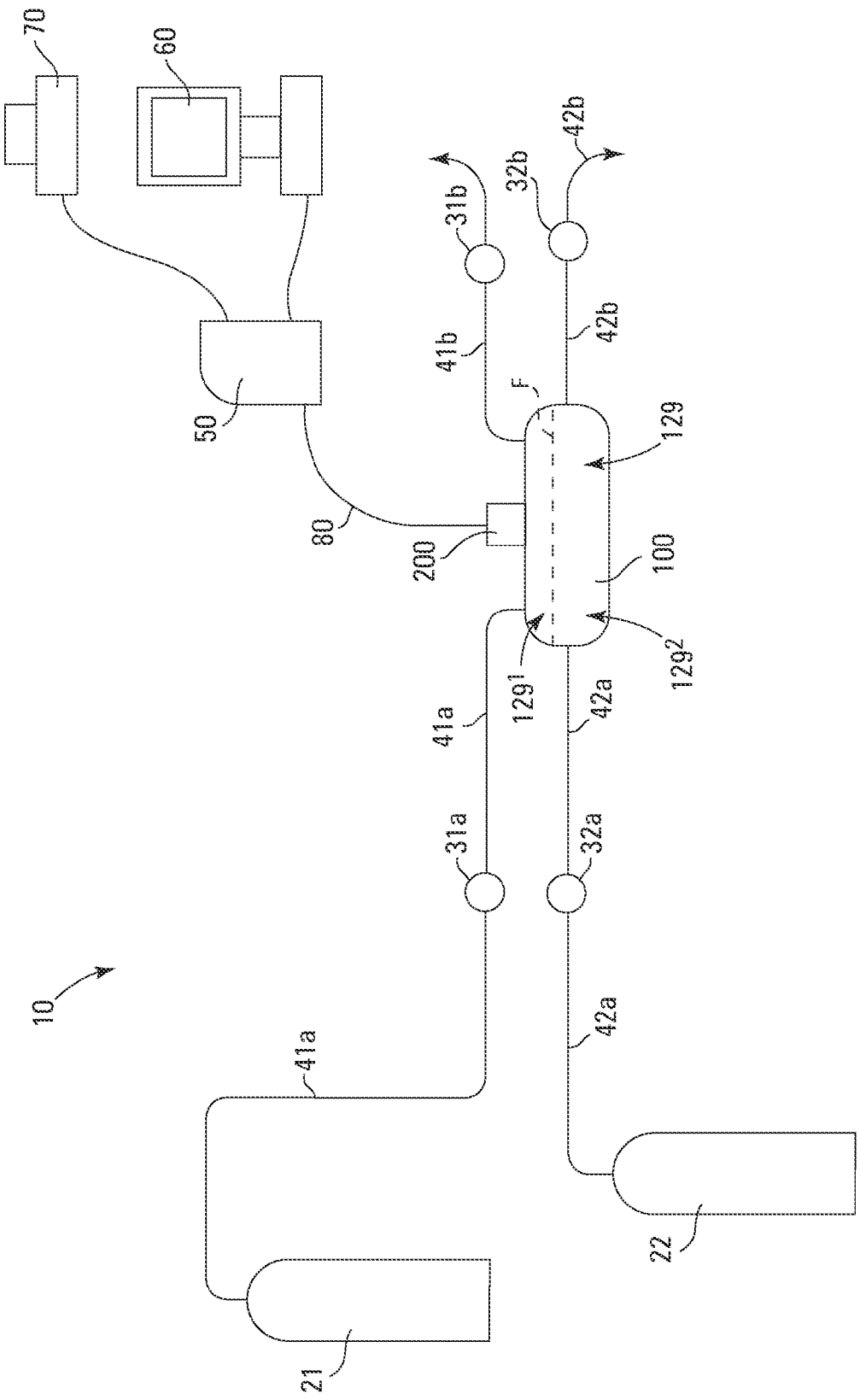
FIG. 1 is a schematic overview of one embodiment of a testing system useful for performing the testing process of the present invention.
Figure 2:
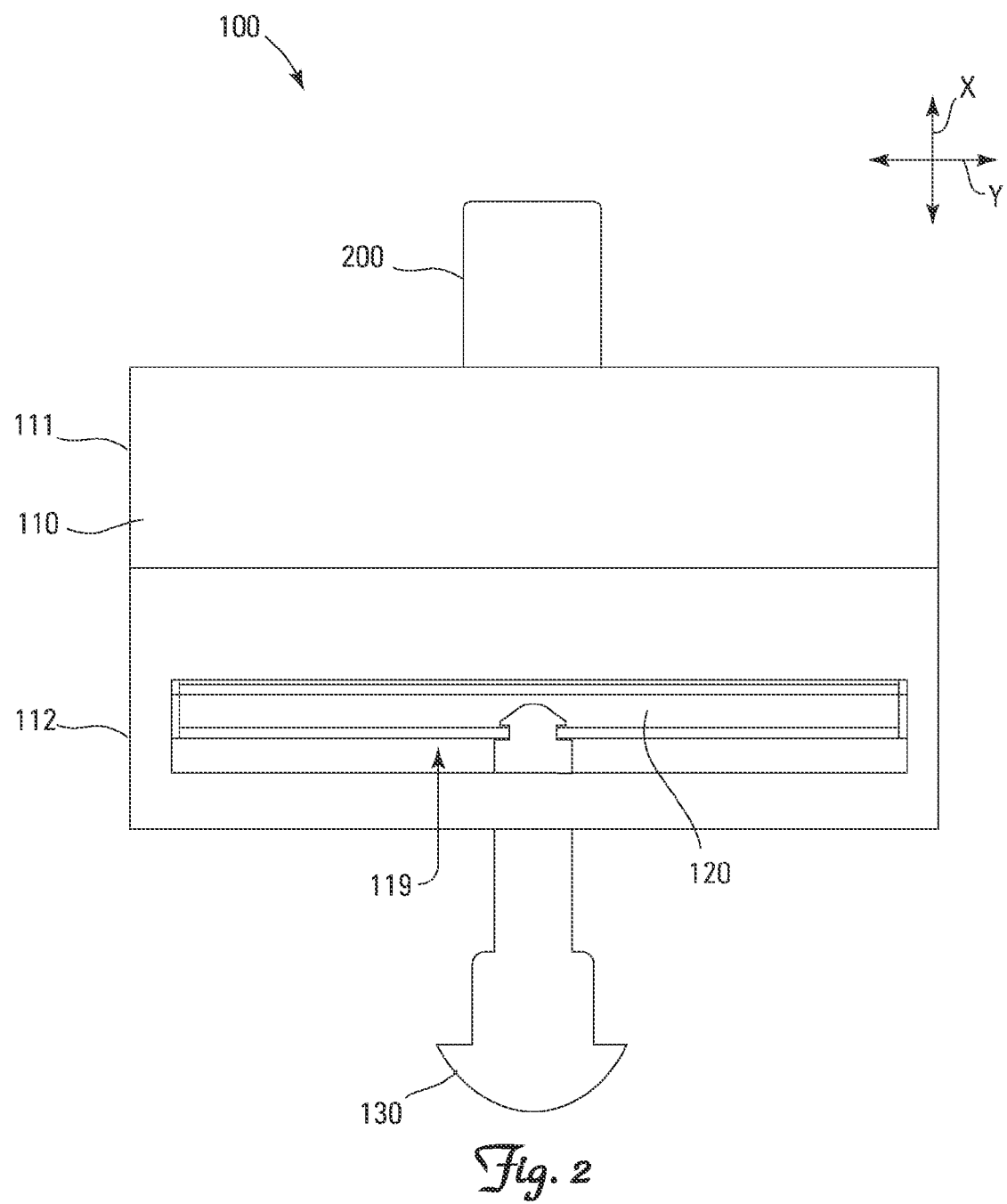
FIG. 2 is a side view of the measurement unit component of the testing system shown in FIG. 1.

Referring generally to FIG. 1, the invention is directed to a method for measuring the transmission rate of an analyte A through a film F. The method includes the steps of (i) separating a testing chamber 129 into a first or upper cell $129^1$ and a second or lower cell $129^2$ with a known area of a film F, (ii) flushing the first cell $129^1$ with an inert gas to remove any target analyte A from the first cell $129^1$, (iii) introducing a gas (not shown) containing a known concentration of an analyte A into the lower cell $129^2$, (iv) sealing the upper cell $129^1$ to gas flow (not shown) through the upper cell $129^1$, and (v) sensing any analyte A in the upper cell $129^1$ with an analyte sensor 200 that consumes the analyte A at a rate greater than the rate at which the analyte A is passing through the film F, until a steady state rate of analyte A consumption is measured by the analyte sensor 200. The analyte sensor 200 preferably consumes analyte A at least ten times faster than the rate at which the analyte A is transmitted through the film F, more preferably twenty times faster, and most preferably one hundred times faster.

The film F can be a perforated or nonperforated film F, and can be porous or nonporous with respect to the target analyte A, so long as the analyte sensor 200 can consume the target analyte A at a rate greater than the rate at which the analyte A is passing through the film F. To ensure that the analyte sensor 200 is consuming all target analyte A that is passing through the film F, the analyte sensor 200 is preferably selected so that it consumes target analyte A at a rate that is at least ten times greater, preferably twenty times greater and most preferably 100 times greater, than the rate at which the target analyte A is likely to be transmitted through the film F.

Specific Embodiment

Testing System
Construction

An exemplary embodiment of a testing system 10 capable of measuring the transmission rate of an analyte A through a film F in accordance with the present invention is depicted in FIG. 1. A measurement unit 100 defines a testing chamber 129 sealingly divided by a film F to be tested into an upper cell $129^1$ and a lower cell $129^2$. A source of an inert gas 21 communicates with the upper cell $129^1$ via inlet conduit 41a and outlet conduit 41b for flushing the upper cell $129^1$ prior to testing. Suitable inert gases include specifically, but not exclusively, nitrogen, argon, helium, krypton or a blend of nitrogen and hydrogen, etc. A source of test gas 22 containing a known concentration of an analyte A, communicates with the lower cell $129^2$ via inlet conduit 42a and outlet conduit 42b for continuously providing the lower cell $129^2$ with test gas to ensure that the concentration of analyte A within the lower cell $129^2$ remains constant throughout a test period. Shutoff valves 31a and 31b are provided in inlet conduit 41a and outlet conduit 41b respectively, for controlling the flow of inert gas through the upper cell $129^1$. Similarly, shutoff valves 32a and 32b are provided in inlet conduit 42a and outlet conduit 42b respectively, for controlling the flow of gas through the lower cell $129^2$.

An analyte sensor 200 for the target analyte A is placed in fluid communication with the upper cell $129^1$ for sensing the presence of target anaylte A within the upper cell $129^1$. Typical target analytes include oxygen, carbon dioxide, carbon monoxide and water vapor. The analyte sensor 200 may be selected from any of the wide variety of commercially available consuming sensors capable of detecting and consuming the target analyte A, with electrochemical sensors generally preferred based upon the high sensitivity and low cost of such sensors and the fact that such sensors, when employed in the present invention, follow Faraday's Law—eliminating the need to calibrate the sensor.

The analyte sensor 200 communicates via electrical leads 80 with a suitable central processing unit 50 equipped with electronic memory (not shown), and optionally but preferably attached to a monitor 60 and/or printer 70 for storing and reporting analyte A concentrations detected by the analyte sensor 200.

Use

A film F to be tested is "loaded" into the testing chamber 129 so as to sealingly separate the testing chamber 129 into an upper cell $129^1$ and a lower cell $129^2$ with a known area of the film F exposed to both cells $129^1$ and $129^2$. Shutoff valves 31a and 31b are then opened to permit the flow of inert gas through the upper cell $129^1$ for flushing analyte A from the upper cell $129^1$. After flushing, the shutoff valves 31a and 31b are closed to seal-off the upper cell $129^1$ from the surrounding environment. Shutoff valves 32a and 32b are then opened to permit the flow of gas containing a known concentration of analyte A into the lower cell $129^2$. The presence of analyte A within the upper cell $129^1$ is then detected and recorded by the analyte sensor 200. By ensuring that the only route through which analyte A can enter into the upper cell $129^1$ is through the "exposed" area of the film F, and by selecting an analyte sensor 200 that consumes analyte A faster than the analyte A is transmitted through the film F, then the rate at which the analyte sensor 200 detects analyte A, once a steady state rate is attained, can be equated directly to the analyte transmission rate for the known "exposed" area of the film F.

Measurement Unit
Construction

An exemplary embodiment of a measurement unit 100 capable of quickly and accurately measuring the transmission rate of an analyte A through a film F in accordance with the present invention is depicted in FIGS. 2-6.

The measurement unit 100 includes (i) a housing 110, (ii) mounting plates 120, (iii) an actuator 130, (iv) a valve 140 for controlling fluid communication with an analyte sensor 200, (v) channels 150 in the housing 110 and mounting plates 120 for directing test gas (not shown) into a lower cell $129^2$ in the mounting plates 120, and (vi) a flow control system (not collectively numbered) including flow control channels 170 and o-ring seals 180 for selectively opening and sealing closing an upper cell $129^1$ in the mounting plates 120 to fluid flow. The measurement unit 100 optionally, but preferably, also includes a humidity control system 190.

The housing 110 includes an upper section 111 and a lower section 112 that cooperatively define a retention chamber 119.

Referring to FIGS. 4A, 4B, 5A, 5B, 6A and 6B, upper and lower mounting plates 121 and 122 (collectively referenced as mounting plates 120) are retained within the retention chamber 119 defined by housing 110 with the upper surface 121$u$ of the upper mounting plate 121 longitudinally y offset a distance from the lower surface 111$i$ of the upper section 111 of the housing 110 so as to define a gap 160 therebetween. The upper and lower mounting plates 121 and 122 define a testing chamber 129 therebetween. An o-ring 125 encircling the testing chamber 129 is provided between the mounting plates 120. The testing chamber 129 can be sealingly divided into an upper cell 129$^1$ and a lower cell 129$^2$ by placement of a test film F between the mounting plates 120 overlaying the o-ring 125, and compressing the mounting plates 120 together so as to sealingly compress the entire periphery of the o-ring 125 between the mounting plates 120.

It is generally preferred to configure the testing chamber 129 to provide an upper cell 129$^1$ of about 1 cm$^3$ to about 3 cm$^3$. An upper cell 129$^1$ larger than about 3 cm$^3$ is too slow to respond as molecules of analyte A within the upper cell 129$^1$ can be consumed and detected by the analyte sensor 200 only when the molecules enter the analyte sensor 200 and the upper cell 129$^1$ relies solely upon diffusion to move molecules within the upper cell 129$^1$. An upper cell 129$^1$ smaller than about 1 cm$^3$ tends to cause areas of the film F to contact with the upper surface (not numbered) of the upper mounting plate 121 during the testing period, thereby introducing error into the test results as analyte A cannot readily pass through the film F into the upper cell 129$^1$ through these "covered" areas.

Referring to FIGS. 4A, 4B, 5A, 5B, 6A and 6B, the lower mounting plate 122 is mounted onto the distal end (unnumbered) of an actuator shaft 131 for longitudinally repositioning of the mounting plates 120 by an actuator 130 as between a lower or open position creating a longitudinally thicker gap 160 between the upper surface 121$u$ of the upper mounting plate 121 and the lower surface 111$i$ of the upper section 111 of the housing 110, as shown in FIGS. 4 (collectively 4A, 4A$^1$, 4A$^2$ and 4A$^3$), and an upper or closed position creating a longitudinally thinner gap 160 between the upper surface 121$u$ of the upper mounting plate 121 and the lower surface 111$i$ of the upper section 111 of the housing 110, as shown in FIGS. 5 (collectively 5A, 5A$^1$, 5A$^2$ and 5A$^3$).

Referring to FIGS. 6A and 6B, fluid flow into the lower cell 129$^2$ is provided by aligned inlet channels 151$a$, 151$b$ and 151$c$ in the upper section 111 of the housing 110, the upper mounting plate 121 and the lower mounting plate 122 respectively. In similar fashion, fluid flow out from the lower cell 129$^2$ is provided by aligned outlet channels 152$a$, 152$b$ and 152$c$ in the upper section 111 of the housing 110, the upper mounting plate 121 and the lower mounting plate 122 respectively. A large diameter o-ring 151$w$ is positioned within the gap 160 encircling the inlet channels 151$a$ and 151$b$ in the upper section 111 of the housing 110 and the upper mounting plate 121 for preventing testing gas from flowing throughout the gap 160. In similar fashion, a large diameter o-ring 152$w$ is positioned within the gap 160 encircling the outlet channels 152$a$ and 152$b$ in the upper section 111 of the housing 110 and the upper mounting plate 121 for preventing testing gas from flowing throughout the gap 160.

Referring to FIGS. 4A and 4B, the flow control system (not collectively numbered) includes (i) flow control channels and passageways 170 through the upper section 111 of the housing 110 and the upper mounting plate 121, and (ii) o-ring seals 180 of different diameters and different thicknesses positioned within the gap 160 and encircling the various channels and passageways 170. The flow control system provides a quick, simple and reliable method of opening and closing the upper cell 129$^1$ and the analyte sensor 200 to fluid flow at the appropriate times.

Referring to FIGS. 4A and 4A$^1$, fluid flow into the upper cell 129$^1$ is provided by laterally x and/or transversely z offset inlet channels 171$a$ and 171$b$ in the upper section 111 of the housing 110 and the upper mounting plate 121 respectively. In similar fashion, referring now to FIGS. 4A and 4A$^2$, fluid flow out from the upper cell 129$^1$ is provided by laterally x and/or transversely z offset outlet channels 172$a$ and 172$b$ in the upper section 111 of the housing 110 and the upper mounting plate 121 respectively.

Referring to FIGS. 4A and 4A$^1$, a small diameter o-ring 181$v$ is positioned within the gap 160 encircling the inlet channel 171$b$ in the upper mounting plate 121. A large diameter o-ring 181$w$ is also positioned within the gap 160 for encircling both the inlet channel 171$a$ in the upper section 111 of the housing 110 and the inlet channel 171$b$ in the upper mounting plate 121 as well as fully encircling the small diameter o-ring 181$v$. In similar fashion, referring now to FIGS. 4A and 4A$^2$, a small diameter o-ring 182$v$ is positioned within the gap 160 encircling the outlet channel 172$b$ in the upper mounting plate 121, with a large diameter o-ring 182$w$ positioned within the gap 160 and encircling both the outlet channel 172$a$ in the upper section 111 of the housing 110 and the outlet channel 172$b$ in the upper mounting plate 121 as well as encircling the small diameter o-ring 182$v$.

Referring to FIGS. 4A, 4A$^1$, 4A$^2$, 4A$^3$, 5A, 5A$^1$, 5A$^2$ and 5A$^3$, the thickness or longitudinal y height of the large diameter o-rings 181$w$ and 182$w$ is selected so that these o-rings 181$w$ and 182$w$ are sealingly engaged within the gap 160 regardless of whether the mounting plates 120 are in the open or closed longitudinally y position so as to prevent fluid from flowing freely within the gap 160. The thickness or longitudinal y height of the smaller diameter o-rings 181$v$ and 182$v$ is selected so that these o-rings 181$v$ and 182$v$ are sealingly engaged within the gap 160 only when the mounting plates 120 are in the closed longitudinally y position. Such positioning of the larger (181$w$ and 182$w$) and smaller (181$v$ and 182$v$) o-rings, in combination with the different thicknesses of the larger (181$w$ and 182$w$) and smaller (181$v$ and 182$v$) o-rings, permits the inlet (171$a$ and 171$b$) and outlet (172$a$ and 172$b$) channels to be simultaneously opened to fluid flow for flushing of the upper cell 129$^1$ prior to a testing period by longitudinally y moving the mounting plates 120 into the downward or open position as shown in FIGS. 4A, 4A$^1$ and 4A$^2$, and simultaneously closed to fluid flow for sealing-off the upper cell 129$^1$ during a testing period by longitudinally y moving the mounting plates 120 into the upward or closed position as shown in FIGS. 4B, 4B$^1$ and 4B$^2$.

Referring to FIGS. 4A, 4A$^3$, 5A and 5A$^3$, the analyte sensor 200 communicates with the upper cell 129$^1$ via longitudinally y aligned passageways 173$a$ and 173$b$ in the upper section 111 of the housing 110 and the upper mounting plate 121 respectively. A large diameter o-ring 183$w$ is positioned within the gap 160 encircling both passageways 173$a$ and 173$b$ for ensuring that fluid diffusing into the analyte sensor 200 from the upper cell 129$^1$ is not contaminated by fluid from the gap 160.

In order to extend the useful life of the analyte sensor 200, especially when an electrochemical sensor is employed, the passageway 173$a$ should be closed at all times except during testing periods (i.e., only after the upper cell 129$^1$ has been flushed with an inert gas and sealed so that the only analyte A in the upper cell $129^1$ is analyte A that has permeated through a test film F). Referring to FIGS. 4A, $4A^3$, 5A and $5A^3$, an expedient technique for providing such limited access to the analyte sensor 200 is to position a normally closed tire valve 140 within the passageway 173a, with the body 141 of the tire valve 140 sealingly wedged into the passageway 173a and the stem 142 of the tire valve 140 extending longitudinally y downward towards the gap 160. An upwardly extending pin 121n is provided on the upper mounting plate 121 for pressing longitudinally y upward against the valve stem 142 and thereby opening the valve 140 only when the mounting plates 120 are in the upper or closed position.

The transmission rate of analyte A through most plastic films F is sensitive to humidity, with an increase in humidity tending to result in an increase in the transmission rate. Most analyte sensors 200 are also somewhat sensitive to humidity, especially if permitted to "dry out". Hence, in order to obtain consistent and comparable test results it is important to maintain a constant relative humidity within the testing chamber 129, especially within the closed upper cell $129^1$. To maintain a constant humidity within the upper cell $129^1$, a humidity control system 190 can be provided. A suitable humidity control system 190 is shown in FIGS. 5A, $5A^1$, 5B and $5B^1$. The humidity control system 190 include a pair of humidity control chambers 199 in the upper mounting plate 121 diametrically positioned relative to the analyte sensor 200 and in fluid communication with both the upper cell $129^1$ and the gap 160. Inlet 191a and outlet 192a channels are provided in the upper section 111 of the housing 110 for placing each of the humidity control chambers 199 in fluid communication with a source of a gas (not shown) having a known humidity, typically 0% or 100% relative humidity. A large diameter o-ring 198w is positioned within the gap 160 encircling each of the humidity control chambers 199 and the corresponding set of inlet 191a and outlet 192a channels. A film 193 permeable to water vapor and impermeable to the target analyte A, such as a Nafion® film, is provided over the opening of each humidity control chamber 199 into the upper cell $129^1$ for purposes of allowing transpiration between the humidity control chamber 199 and the upper cell $129^1$ without introducing extraneous analyte A into the upper cell $129^1$ or allowing analyte A to escape from the upper cell $129^1$ undetected. The selectively permeable film 193 can be sealingly held in position within each humidity control chamber 199 by an o-ring 194, washer 195, inset ring 196 and locking ring 197 as shown in FIGS. $5A^1$ and $5B^1$.

Use

The mounting plates 120 are removed from the retention chamber 129 by activating the actuator 130 to lower the actuator shaft 131 into a removal position (not shown) where the o-ring seals 180 within the gap 160 no longer contact the upper section 111 of the housing 110, and sliding the mounting plates 120 out through an open side (not numbered) of the lower section 112 of the housing 110.

The upper mounting plate 121 is then separated from the lower mounting plate 122, and a sample of the film F to be tested placed atop the lower mounting plate 122 over the test chamber 129 so as to fully engage the entire periphery of the o-ring 125 encircling the test chamber 129.

The upper mounting plate 121 is then placed back atop the lower mounting plate 122 and secured to the lower mounting plate 122 so as to sealingly clamp the film F between the plates 121 and 122, thereby sealingly separating the testing chamber 129 into an upper cell $129^1$ and a lower cell $129^2$ with a known area of the film F exposed to both cells $129^1$ and $129^2$. The "loaded" mounting plates 120 are then slid back into the retention chamber 119.

Referring to FIGS. 4A, $4A^1$, $4A^2$ and $4A^3$, the actuator 130 is activated to move the loaded mounting plates 120 into an "open" position wherein the larger diameter o-rings 181w, 182w, 183w and 198w located within the gap 160 sealingly engage the lower surface 111i of the upper section 111 of the housing 110 while the smaller diameter o-rings 181v and 182v within the gap 160 do not. With the mounting plates 120 in the "open" position, the upper cell $129^1$ is flushed with an inert gas to remove any target analyte A from the upper cell $129^1$ by placing the inlet channel 171a in the upper section 111 of the housing 110 in fluid communication with a pressurized source of inert gas 21 and allowing the inert gas to flow sequentially through the inlet channel 171a in the upper section 111 of the housing 110, through that portion of the gap 160 surrounded by the larger diameter o-ring 181w, through the inlet channel 171b in the upper mounting plate 121, through the upper cell $129^1$, through the outlet channel 172b in the upper mounting plate 121, through that portion of the gap 160 surrounded by the larger diameter o-ring 182w, and out from the measurement unit 100 through the outlet channel 172a in the upper section 111 of the housing 110.

Referring to FIGS. 4B, $4B^1$, $4B^2$ and $4B^3$, after flushing, the actuator 130 is activated to move the loaded mounting plates 120 into a "closed" position wherein both the larger diameter o-rings 181w, 182w, 183w and 198w and smaller diameter o-rings 181v and 182v within the gap 160 sealingly engage the lower surface 111i of the upper section 111 of the housing 110 so as to seal-off the upper cell $129^1$ from the surrounding environment.

Referring to FIG. $4A^3$, movement of the loaded mounting plates 120 into the "closed" position also causes the pin 121n on the upper mounting plate 121 to engage the stem 142 on the valve 140 within the passageway 173a in the upper section 111 of the housing 110 so as to open the passageway 173a and thereby place the analyte sensor 200 in fluid communication with the upper cell $129^1$.

With the mounting plates 120 in the "closed" position, the lower cell $129^2$ is flushed with a test gas containing a known concentration of target analyte A and continuously supplied with "fresh" test gas throughout the testing period to ensure that the concentration of target analyte A within the lower cell $129^1$ remains constant. Test gas is introduced into the lower cell $129^2$ by placing the inlet channel 151a in the upper section 111 of the housing 110 in fluid communication with a pressurized source of test gas 22 and allowing the test gas to flow sequentially through the inlet channel 151a in the upper section 111 of the housing 110, through that portion of the gap 160 surrounded by the larger diameter o-ring 151w, through the inlet channel 151b in the upper mounting plate 121, through the inlet channel 151c in the lower mounting plate 122, through the lower cell $129^2$, through the outlet channel 152c in the lower mounting plate 122, through the outlet channel 152b in the upper mounting plate 121, through that portion of the gap 160 surrounded by the larger diameter o-ring 152w, and out from the measurement unit 100 through the outlet channel 152a in the upper section 111 of the housing 110.

Target analyte A will permeate through the film F as the analyte A seeks to diffuse through the film F from a region of higher concentration (i.e., the lower cell $129^2$) to a region of lower concentration (i.e., the upper cell $129^1$). Since test gas continuously flows through the lower cell $129^2$ the concentration of target analyte A in the region of higher concentration remains constant throughout the relevant test period. Similarly, since the analyte sensor 200 consumes target analyte A within the upper cell $129^1$ faster that the target analyte A permeates through the film F, the concentration of target analyte A in the region of lower concentration also remains constant at essentially zero throughout the relevant test period.

Eventually, the system will reach a steady state condition where the rate at which analyte A is detected in the upper cell 129[1] by the analyte sensor 200 and reported by the central processing unit 50 remains constant. This steady state rate equates directly to the permeation rate for the film F for the "exposed" area of the film.

EXAMPLES

Example 1

A 1.0 mil thick polyethylene terephthalate mylar film is placed between the mounting plates of the permeation testing system depicted in FIGS. 1-7 so as to provide a 50 cm$^2$ area of the film exposed to both the upper and lower cells. Permeation testing is conducted in accordance with ASTM D3985 employing the following testing parameters:

| Gas In Upper Cell: | |
|---|---|
| Type: | 100% $N_2$ |
| RH: | 10% |
| Gas In Lower Cell: | |
| Type: | 100% $O_2$ |
| RH: | 10% |
| Testing Chamber Temp: | 23° C. |
| Barometer: | 742.3 mmHg |

Oxygen within the upper cell is continuously sensed with a high-sensitivity standard electrochemical oxygen sensor covered with a porous membrane. Utilizing a reporting cycle of five (5) minutes, the transmission rate of oxygen through the film (O2TR) is calculated from the amperes sensed by the sensor each reporting cycle utilizing EQUATION A. The O2TR calculated for each reporting cycle throughout the testing period is graphically depicted in FIG. 8 and set forth in Table One below. The O2TR for the film, reported after fifty (50) reporting cycles (4 hours and 10 minutes) is 60.975 cm$^3$/(m$^2$)(day).

$$O2TR = Amperes/(Area)(k_1)(k_2)(k_3) \quad \text{(EQUATION A)}$$

Wherein:
O2TR=Transmission Rate of Oxygen (cm$^3$/(m$^2$)(sec))
Amperes=Amperes generated at the sensor (coulombs/second)
Area=Exposed area of the film (m$^2$)
$k_1$=Molecules of Oxygen per cm$^3$ at Standard Temperature and Pressure (2.6876*10$^{19}$ molecules/cm$^3$)
$k_2$=Electrons involved in covalent bonding @ the sensor per molecule of Oxygen (4 e-/molecule)
$k_3$=Coulombs generated per electron (1.6*10$^{-19}$ coulombs/e-)

TABLE ONE

| Time (hrs:min) | O2TR cm$^3$/(m$^2$)(day) |
|---|---|
| 5 | 0.1 |
| 10 | 5.078 |
| 15 | 15.105 |
| 20 | 25.023 |
| 25 | 33.235 |
| 30 | 39.666 |

TABLE ONE-continued

| Time (hrs:min) | O2TR cm$^3$/(m$^2$)(day) |
|---|---|
| 35 | 47.96 |
| 40 | 51.218 |
| 45 | 53.614 |
| 50 | 55.399 |
| 55 | 56.72 |
| 1:00 | 57.732 |
| 1:05 | 58.499 |
| 1:10 | 59.073 |
| 1:15 | 59.491 |
| 1:20 | 59.844 |
| 1:25 | 60.086 |
| 1:30 | 60.254 |
| 1:35 | 60.397 |
| 1:40 | 60.51 |
| 1:45 | 60.592 |
| 1:50 | 60.67 |
| 1:55 | 60.715 |
| 2:00 | 60.769 |
| 2:05 | 60.785 |
| 2:10 | 60.807 |
| 2:15 | 60.84 |
| 2:20 | 60.857 |
| 2:25 | 60.843 |
| 2:30 | 60.858 |
| 2:35 | 60.858 |
| 2:40 | 60.896 |
| 2:45 | 60.9 |
| 2:50 | 60.935 |
| 2:55 | 60.952 |
| 3:00 | 60.957 |
| 3:05 | 60.973 |
| 3:10 | 60.97 |
| 3:15 | 60.966 |
| 3:20 | 60.954 |
| 3:25 | 60.959 |
| 3:30 | 60.948 |
| 3:35 | 60.98 |
| 3:40 | 60.984 |
| 3:45 | 60.978 |
| 3:50 | 60.974 |
| 3:55 | 60.973 |
| 4:00 | 60.984 |
| 4:05 | 60.968 |
| 4:10 | 60.975 |

We claim:

1. A method for measuring the transmission rate of an analyte through a film, comprising:
    (a) separating a chamber into a first cell and a second cell with a known area of a film,
    (b) introducing a gas containing a known concentration of an analyte into the second cell,
    (c) sealing the first cell to gas flow through the first cell,
    (d) sensing any analyte in the sealed first cell with a sensor that consumes the analyte at a rate greater than the rate at which the analyte is passing through the film, until a steady state rate of analyte consumption is measured by the sensor.

2. The method of claim 1 further comprising the step of dividing the steady state rate of analyte consumption measured by the sensor by the known area of the film and reporting this value as the transmission rate of the analyte through the film.

3. The method of claim 1 wherein the analyte is oxygen.

4. The method of claim 1 wherein the analyte is carbon dioxide.

5. The method of claim 1 wherein the analyte is carbon monoxide.

6. The method of claim 1 wherein the analyte is moisture vapor.

7. The method of claim 1 wherein the film is perforated.

8. The method of claim 1 wherein the film is porous with respect to the analyte.

9. The method of claim 1 wherein the film is nonporous with respect to the analyte.

10. The method of claim 1 wherein the first cell has a volume of less than about 3 $cm^3$.

11. The method of claim 1 wherein gas containing a known concentration of the analyte continuously flows through the second cell throughout step (d).

12. The method of claim 1 wherein the sensor is an electrochemical sensor.

13. The method of claim 1 wherein the sensor is a membrane-covered electrochemical sensor wherein the membrane is porous or nonporous.

14. The method of claim 1 wherein the sensor consumes the analyte at a rate that is at least ten times greater than the rate at which the analyte is transmitted through the film.

15. The method of claim 1 wherein the sensor consumes the analyte at a rate that is at least twenty times greater than the rate at which the analyte is transmitted through the film.

16. The method of claim 1 wherein the sensor consumes the analyte at a rate that is at least one hundred times greater than the rate at which the analyte is transmitted through the film.

* * * * *